US009925305B2

(12) United States Patent
Anderson et al.

(10) Patent No.: US 9,925,305 B2
(45) Date of Patent: Mar. 27, 2018

(54) APPARATUS AND METHOD FOR HYDRATING A PARTICULATE BIOMATERIAL WITH A LIQUID BIOMATERIAL

(71) Applicant: NORDSON CORPORATION, Westlake, OH (US)

(72) Inventors: Benjamin B. Anderson, Wheeling, IL (US); Kevin C. Geppert, Eagan, MN (US); Thomas A. Kirk, Hastings, MN (US); Huadong Lou, Plymouth, MN (US); Mark Stevenson, Cottage Grove, MN (US)

(73) Assignee: Nordson Corporation, Westlake, OH (US)

( * ) Notice: Subject to any disclaimer, the term of this patent is extended or adjusted under 35 U.S.C. 154(b) by 0 days.

(21) Appl. No.: 15/419,062

(22) Filed: Jan. 30, 2017

(65) Prior Publication Data

US 2017/0136151 A1 May 18, 2017

Related U.S. Application Data

(62) Division of application No. 14/206,586, filed on Mar. 12, 2014, now Pat. No. 9,592,321.

(Continued)

(51) Int. Cl.

*B01F 5/06* (2006.01)
*A61L 27/36* (2006.01)

(Continued)

(52) U.S. Cl.

CPC ...... *A61L 27/3691* (2013.01); *A61B 17/8827* (2013.01); *A61J 1/2096* (2013.01);

(Continued)

(58) Field of Classification Search

CPC ..................................... B01F 5/06; A61J 1/20

See application file for complete search history.

(56) References Cited

U.S. PATENT DOCUMENTS 4,423,741 A 1/1984 Levy
7,637,279 B2 * 12/2009 Amley ............. A61M 5/14216 137/102

(Continued)

FOREIGN PATENT DOCUMENTS

DE 102007049123 A1 4/2009
EP 0495419 A2 7/1992

(Continued)

OTHER PUBLICATIONS

European Patent Office, European Search Report in EP Application No. 14159987, dated Nov. 3, 2014.

(Continued)

*Primary Examiner* — Cachet I Sellman

(74) *Attorney, Agent, or Firm* — Baker & Hostetler LLP

(57) ABSTRACT

An apparatus and method for hydrating a particulate biomaterial with a liquid biomaterial includes a vacuum device and a valve for withdrawing a gas from the particulate biomaterial and introducing the liquid biomaterial. The valve includes a hub, a valve body, a particulate port, a vacuum port, and a liquid port. The valve body selectively moves between first and second positions. The valve body at least partially defines a first passage and a second passage. The particulate port, the vacuum port, and the liquid port are each configured to fluidly connect to a particulate container, the vacuum device, and the liquid container, respectively. In the first position, the first passage fluidly connects the vacuum port to the particulate port for withdrawing the gas from the particulate container. In the second position, the (Continued)

second passage fluidly connects the liquid port to the particulate port for hydrating the particulate biomaterial.

20 Claims, 12 Drawing Sheets

Related U.S. Application Data

(60) Provisional application No. 61/794,743, filed on Mar. 15, 2013.

(51) Int. Cl.

| | |
|---|---|
| ***A61B 17/88*** | (2006.01) |
| ***A61M 39/22*** | (2006.01) |
| ***A61J 1/20*** | (2006.01) |
| ***B01F 3/20*** | (2006.01) |
| ***B01F 3/12*** | (2006.01) |
| ***B01F 13/00*** | (2006.01) |
| ***B01F 15/02*** | (2006.01) |

(52) U.S. Cl.

CPC ......... *A61M 39/223* (2013.01); *B01F 3/1214* (2013.01); *B01F 3/1228* (2013.01); *B01F 3/2021* (2013.01); *B01F 13/0023* (2013.01); *B01F 15/0225* (2013.01); *B01F 15/0258* (2013.01); *A61J 1/2062* (2015.05); *A61J 1/2072* (2015.05); *A61L 2430/02* (2013.01); *A61M 2039/229* (2013.01); *B01F 2215/0034* (2013.01)

(56) References Cited

U.S. PATENT DOCUMENTS

| | | | | |
|---|---|---|---|---|
| 9,402,786 | B2 | 8/2016 | Petrone | |
| 2001/0016703 | A1 | 8/2001 | Wironen et al. | |
| 2002/0017328 | A1 | 2/2002 | Loo | |
| 2004/0232163 | A1 | 11/2004 | Reinsch et al. | |
| 2012/0071884 | A1 * | 3/2012 | Cooper .............. | A61B 17/8827 606/93 |
| 2014/0251438 | A1 * | 9/2014 | Gettings ............... | B01F 5/0685 137/1 |

FOREIGN PATENT DOCUMENTS

| | | | |
|---|---|---|---|
| EP | 1627658 | A1 | 2/2006 |
| GB | 2458572 | A | 9/2009 |
| WO | WO2007084214 | A1 | 7/2007 |

OTHER PUBLICATIONS

European Patent Office, Partial European Search Report in EP Application No. 14159987, dated Jul. 17, 2014.

* cited by examiner

APPARATUS AND METHOD FOR HYDRATING A PARTICULATE BIOMATERIAL WITH A LIQUID BIOMATERIAL

CROSS-REFERENCE TO RELATED APPLICATION

This application is a divisional application of U.S. patent application Ser. No. 14/206,586, filed Mar. 12, 2014, and published as U.S. Patent App. Pub. No. 2014/0261082 on Sep. 18, 2014, which claims the priority of U.S. Provisional Patent App. No. 61/794,743, filed Mar. 15, 2013, the disclosures of which are hereby incorporated by reference herein.

TECHNICAL FIELD

The present invention relates generally to an apparatus and method for hydrating a particulate biomaterial with a liquid biomaterial, and more particularly, to an apparatus and method for hydrating a bone graft particulate material with a liquid bone graft biomaterial.

BACKGROUND

Bone grafting is a surgical procedure for repairing bones and typically involves introducing a mixture of particulate, such as bone graft material, into an area of bone that requires repair, such as a fracture. The bone graft material is intended to stimulate growth of healthy native bone tissue, and new native bone tissue may eventually replace the bone graft material completely. Bone graft material is a type of biomaterial and typically includes a combination of crushed bone and a liquid component, such as blood, plasma, or growth factors. Bone graft materials can be allograft (derived from a human other than the one receiving the graft), autograft (derived from the human receiving the graft), and synthetic (created from, for example, ceramics like calcium phosphates).

Bone graft materials are typically delivered to a surgical site using syringe-like delivery devices, which often include attachments, such as small diameter cannulae. In addition, the components of the bone graft material are sometimes brought together and combined to form the mixture of the bone graft material in the delivery device. However, the mixture of the bone graft material tends to also include gas from the porosity of the crushed bone and the aeration associated with mixing the components. As the bone graft materials dry after being applied to the surgical site, a portion of the gas collects into pockets within the setting bone graft material. The pockets create inconsistencies in the final bone graft material that may result in performance variation throughout the bone graft material.

Furthermore, hydrating the particulate biomaterial with the liquid biomaterial requires additional time for the liquid biomaterial to displace the gas and disperse throughout the entirety of the particulate biomaterial. At the very least, this additional time increases the cost of the medical procedure. In addition, a relatively fine particulate biomaterial tends to non-uniformly absorb the liquid component, which requires additional blending to mix the particulate and liquid biomaterial to a generally uniform mixture.

There is a need for an apparatus and method for hydrating a particulate biomaterial with a liquid biomaterial, such as a particulate and liquid bone graft materials, that reduces the gas within the mixture and addresses present challenges and characteristics such as those discussed above.

SUMMARY

An exemplary embodiment of an apparatus for hydrating a particulate biomaterial with a liquid biomaterial includes a vacuum device configured to generate a vacuum and a valve for withdrawing a gas from the particulate biomaterial and introducing the liquid biomaterial to the particulate biomaterial. The valve includes a hub, a valve body, a particulate port, a vacuum port, and a liquid port. The valve body is movably coupled with the hub and configured to selectively move between a first position and a second position. The valve body at least partially defines a first passage and a second passage. The particulate port is configured to fluidly connect to a particulate container holding the particulate biomaterial therein. The vacuum port is configured to fluidly connect to the vacuum device such that the first passage fluidly connects the vacuum port to the particulate port when the valve body is in the first position for withdrawing the gas from the particulate container. The liquid port is configured to fluidly connect to a liquid container holding the liquid biomaterial therein. As such, the second passage fluidly connects the liquid port to the particulate port when the valve body is in the second position for withdrawing the liquid biomaterial from the liquid container, through the second passage, and to the particulate container for hydrating the particulate biomaterial.

An exemplary embodiment of a valve for withdrawing a gas from a particulate biomaterial and introducing a liquid biomaterial to the particulate biomaterial includes a hub, a valve body, a particulate port, a vacuum port, and a liquid port. The valve body is movably coupled with the hub and configured to selectively move between a first position and a second position. The valve body at least partially defines a first passage and a second passage. The particulate port is configured to fluidly connect to a particulate container holding the particulate biomaterial therein. The vacuum port is configured to fluidly connect to the vacuum device such that the first passage fluidly connects the vacuum port to the particulate port when the valve body is in the first position for withdrawing the gas from the particulate container. The liquid port is configured to fluidly connect to a liquid container holding the liquid biomaterial therein. As such, the second passage fluidly connects the liquid port to the particulate port when the valve body is in the second position for withdrawing the liquid biomaterial from the liquid container, through the second passage, and to the particulate container for hydrating the particulate biomaterial.

In use, a method of hydrating a particulate biomaterial with a liquid biomaterial to form a mixture of biomaterials includes a vacuum device and a valve. The particulate biomaterial is held within a particulate container and the liquid biomaterial is held within a liquid container. The valve is fluidly connected to the particulate container, the liquid container, and the vacuum device. The valve has a valve body selectively movable between a first position and a second position. The method includes generating a vacuum within the particulate container with the vacuum device when the valve body is in the first position. The method also includes withdrawing a gas from the particulate container and through the valve body toward the vacuum device to maintain the vacuum within the particulate container. In addition, the method includes moving the valve body to the second position such that the liquid container fluidly connects to the particulate container via the valve body. The method further includes releasing the vacuum within the particulate container to the liquid container to withdraw the liquid biomaterial from the liquid container and introduce the liquid biomaterial into the particulate container. The method also includes hydrating the particulate biomaterial with the liquid biomaterial to form the mixture of biomaterials.

Various additional objectives, advantages, and features of the invention will be appreciated from a review of the following detailed description of the illustrative embodiments taken in conjunction with the accompanying drawings.

BRIEF DESCRIPTION OF THE DRAWINGS

The accompanying drawings, which are incorporated in and constitute a part of this specification, illustrate embodiments of the invention and, together with a general description of the invention given above, and the detailed description given below serve to explain the invention.

DETAILED DESCRIPTION

Figure 1:
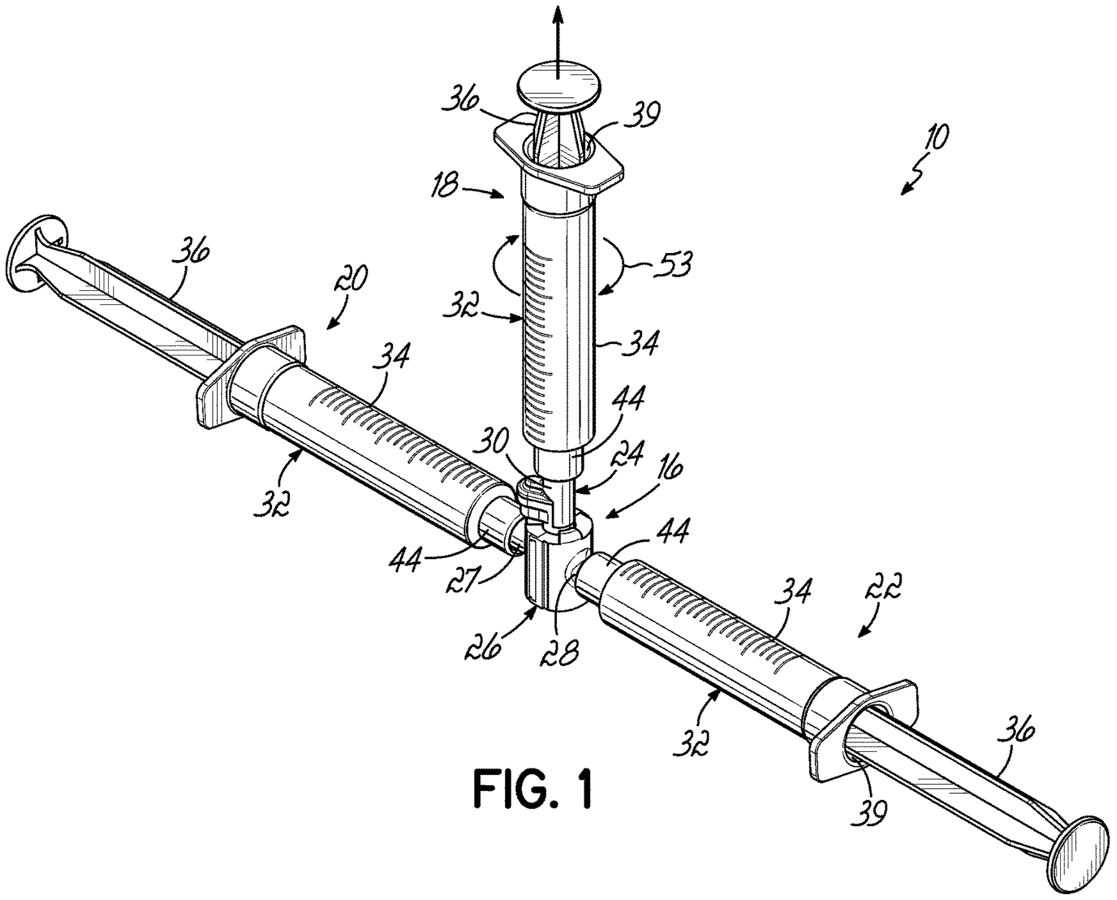
FIG. 1 is a perspective view of an embodiment of an apparatus having a first embodiment of a valve for hydrating a particulate bone graft material with a liquid bone graft material.
Figure 2:
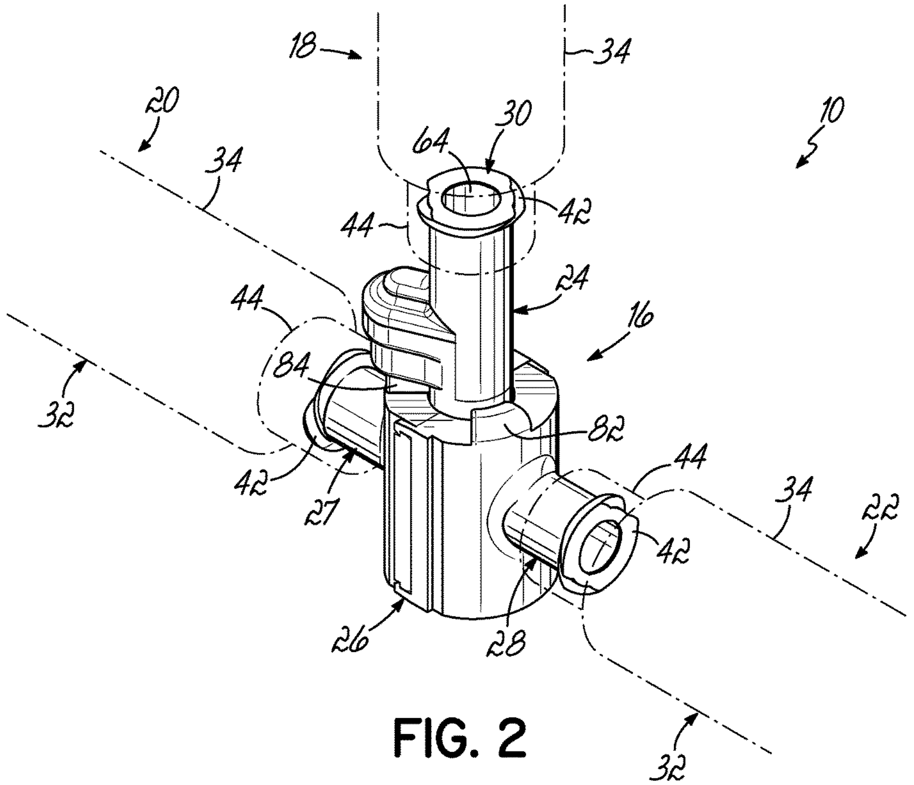
FIG. 2 is perspective view of the valve of FIG. 1.
Figure 3:
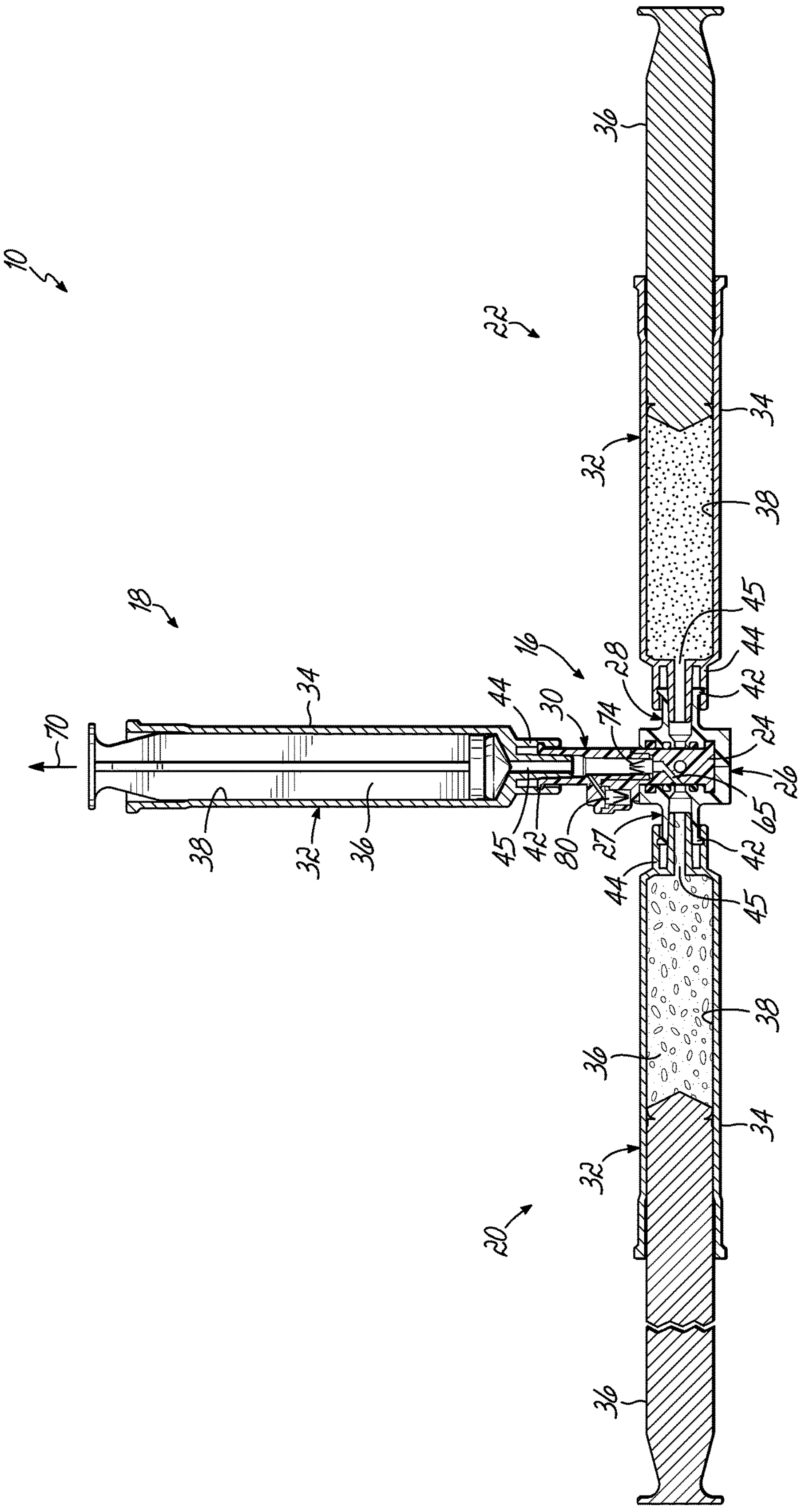
FIG. 3 is a cross-section view of FIG. 1.

With reference to FIGS. 1-3, a first embodiment of an apparatus 10 for hydrating a particulate biomaterial with a liquid biomaterial includes a valve 16 fluidly connected to a vacuum device 18, a particulate container 20, and a liquid container 22. The particulate container 20 holds the particulate biomaterial, while the liquid container 22 holds the liquid biomaterial. The valve 16 includes a valve body 24 movably coupled with a hub 26 and, as such, selectively moves between a first position and a second position. According to an exemplary embodiment, the hub 26 includes a particulate port 27 and an opposing liquid port 28, both of which are configured to removably connect to the particulate container 20 and liquid container 22, respectively. The valve body 24 includes a vacuum port 30 configured to removably connect to the vacuum device 18 for generating a vacuum therein. In the first position, the vacuum device 18 is configured to withdraw a gas from the particulate biomaterial, while the valve 16 maintains the vacuum within the particulate container 20. Once a desirable amount of the gas is removed from the particulate container 20, a practitioner, such as a doctor, nurse, or similarly trained medical professional, selectively moves the valve body 24 to the second position, which fluidly connects the particulate container 20 to the liquid container 22. In turn, the valve 16 operatively releases the vacuum to the liquid container 22 and withdraws the liquid biomaterial into the particulate container 20 for hydrating the particulate biomaterial therein. As described herein, the particulate and liquid biomaterial may be any biomaterial component, such as dry particulate component and/or a liquid biomaterial component, respectively. According to an exemplary embodiment, the particulate biomaterial is a dry bone graft biomaterial component, such as an allograft, autograft, or synthetic biomaterial material, and the liquid biomaterial is a bone graft biomaterial component, such as blood, plasma, or growth factors. However, it will be appreciated that the apparatus 10 may be used to hydrate any particulate material with a liquid material and is not intended for use only with bone graft biomaterials.

According to an exemplary embodiment, the vacuum device 18 is in the form of a syringe 32 including a syringe body 34 and a plunger 36. The generally cylindrical syringe body 34 defines a cavity 38 extending therethrough, which slidably receives the plunger 36 through a distal opening 39. The syringe 32 also includes a proximal opening 40 (see FIG. 4A) in fluid communication with the vacuum port 30. With respect to the use of the terms "distal" and "proximal," it will be appreciated that such directions are intended to describe relative locations along exemplary embodiments of the apparatus 10. More particularly, the term "distal" refers to relative positions away from the valve 16, whereas the term "proximal" refers to relative positions near the valve 16. It is not intended that the terms "distal" and "proximal" limit the invention to any of the exemplary embodiments described herein. Furthermore, the particulate container 20 and liquid container 22 are also in the form of syringes 32 that similarly include additional syringe bodies 34 and plungers 36. However, it will be appreciated that any vacuum device 18 and containers for holding particulate and liquid biomaterial may be similarly used. By way of example, one or both of the particulate and liquid containers 20, 22 may alternatively be in the form of a collapsible container, such as a sealable bag. As such, it is not intended to limit the vacuum device 18, the particulate container 20, and the liquid container 22 to the embodiments described herein.

The syringe body 34 is generally transparent for viewing any contents within the cavity 38. Of course, it will be appreciated that the syringe 32 may alternatively be translucent for viewing the contents therein. Each of the particulate, liquid, and vacuum ports 27, 28, 30 includes a coupling

42, which may be in the form of a male coupling 42. In addition, the syringe 32 also includes female coupling 44 that cooperates with the male couplings 42 for fluidly connecting each syringe 32 to the valve 16 via a hole 45 extending proximally from the syringe body 34 toward the valve body 24. According to an exemplary embodiment, the male and female couplings 42, 44 are in the form of male and female luer couplings, respectively. However, it will be appreciated that any structure for fluidly connecting the vacuum device 18, the particulate container 20, and the liquid container 22 to the valve 16 may be similarly used.

Figure 4A:
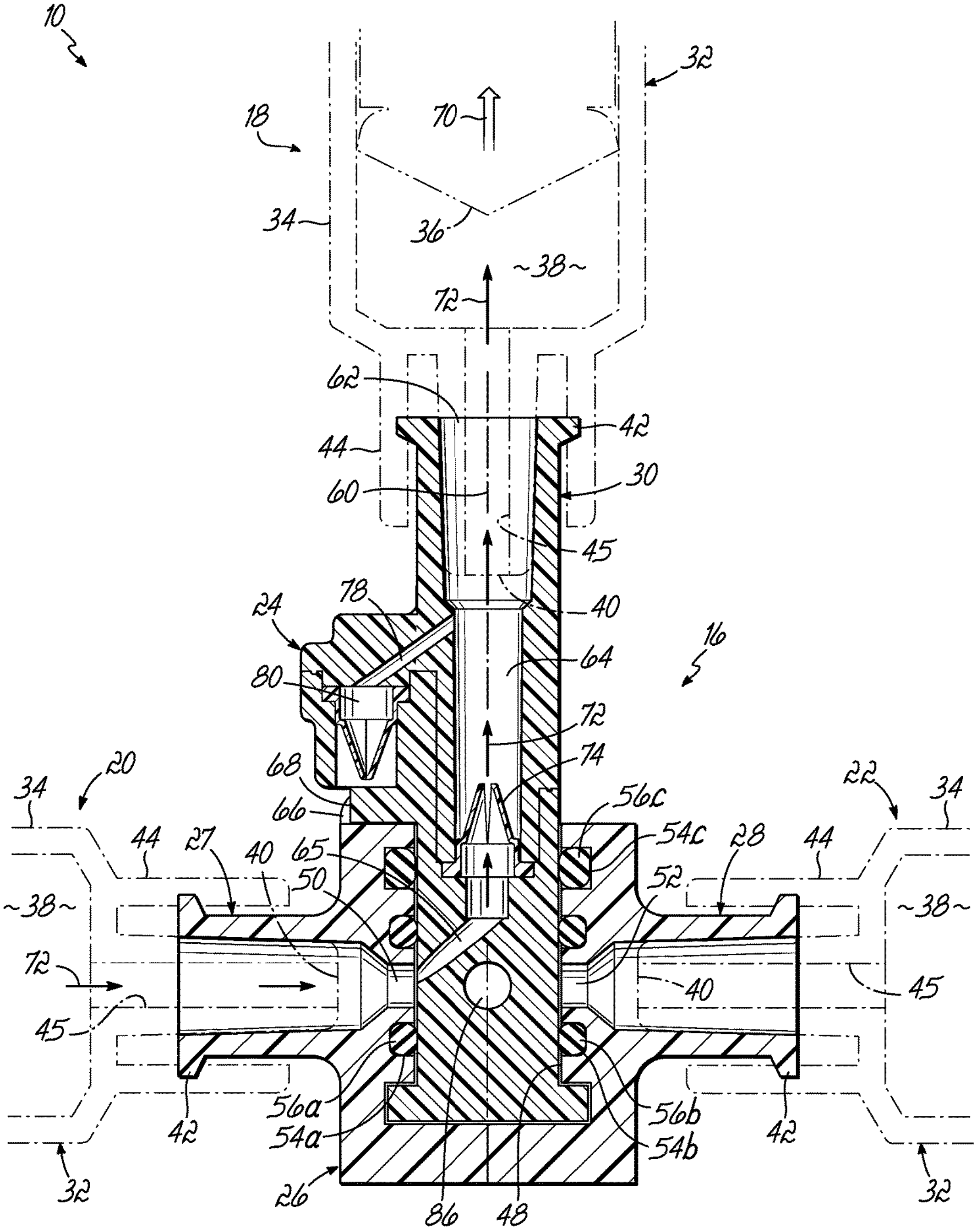
FIG. 4A is an enlarged cross-section view similar to FIG. 3 with the valve having a valve body in a first position for withdrawing a gas from a particulate container.

As described briefly above and with respect to FIG. 1 and FIG. 4A, the valve 16 includes the valve body 24 selectively movable between the first position and the second position relative to the hub 26. The hub 26 surrounds a portion of the valve body 24 such that vacuum port 30 projects distally from the hub 26 and toward the vacuum device 18. More particularly, the hub 26 defines an aperture 48 that receives and captures the valve body 24 and defines a particulate bore 50 and a liquid bore 52, both of which extend through the hub 26 generally transverse to the aperture 48. The particulate bore 50 extends from the particulate port 27 to the aperture 48, and the liquid bore 52 similarly extends from the liquid port 28 to the aperture 48. While the valve body 24 is captured within the hub 26, the valve body 24 is still free to rotate a first direction, as indicated by arrow 53, toward the first position and a second direction toward the second position. According to an exemplary embodiment, the first direction is clockwise and the second direction is counterclockwise. However, these exemplary directions are not intended to limit the invention described herein.

To inhibit leakage between the hub 26 and the valve body 24 and into the aperture 48, an exemplary embodiment of the hub 26 also includes a plurality of annular recesses 54*a*, 54*b*, 54*c* that cooperates with a plurality seals 56*a*, 56*b*, 56*c*. The annular recesses 54*a*, 54*b* generally surround the particulate and liquid bores 50, 52, respectively, and extend to the aperture 48 within the hub 26. The annular recess 54*c* is generally transverse to the annular recess 54*a*, 54*b* and surrounds the valve body 24 within the aperture 48. As such, the annular recesses 54*a*, 54*b*, 54*c* receive the seals 56*a*, 56*b*, 56*c* for sealing the particulate, liquid, and vacuum ports 27, 28, 30 from each other and inhibiting the vacuum, the particulate biomaterial, and the liquid biomaterial from leaking into the aperture 48 and/or into the ambient environment. It will be appreciated that the valve body 24 may move between the first and second positions by rotating, as discussed further below, or by any other movement. For example, the valve body 24 may alternatively linearly translate as will be described later in further detail. The following will address additional structure of the valve body 24 with respect to the first position and the second position.

FIG. 4A shows the apparatus 10 having the valve body 24 in the first position. The valve body 24 extends along a rotational axis 60 and includes a distal opening 62 that opens into the vacuum port 30. Specifically, the vacuum port 30 extends along and parallel to the rotational axis 60. The valve body 24 further defines a first conduit 64 that extends from the vacuum port 30 to the particulate bore 50 for fluid communication with the particulate port 27. As such, the vacuum port 30 and the particulate port 27 are fluidly connected only when the valve body 24 is in the first position. As discussed above, the valve body 24 is already in the first position and, as such, the vacuum port 30, the first conduit 64, the particulate bore 50, and the particulate port 27 collectively define a first passage 65 extending from the vacuum device 18 to the particulate container 20. However, in the event that the valve body 24 is not in the first position, the hub 26 includes a first abutment member 66 projecting distally toward the valve body 24 that cooperates with a first stop surface 68 for positioning the valve body 24. More particularly, the valve body 24 rotates the clockwise direction 53 (see FIG. 1) until the first stop surface 68 contacts the first abutment member 66 such that the first conduit 64 rotatably aligns to fluidly connect to the particulate port 27 and define the first passage 65.

Once the vacuum port 30 is fluidly connected to the particulate port 27 via the first conduit 64, the plunger 36 is withdrawn within the syringe body 34 of the vacuum device 18, as indicated by arrow 70 and also referred to herein as a vacuum stroke 70. In turn, the vacuum device 18 generates a vacuum, which withdraws the gas from the particulate container 20, as indicated by arrows 72. A first check valve 74 is also positioned within the first passage 65 for inhibiting the gas from returning to the particulate container 20. The first check valve 74 is mounted within the first conduit 64 of the valve body 24. At this position, the first check valve 74 is operable to open and close by the pressure differential between the vacuum port 30 and particulate port 27. In the event that the pressure in the vacuum port 30 is less than the pressure in the particulate port 27, the first check valve 74 selectively opens for withdrawing gas from the particulate container 20. However, in the event that the pressure in the vacuum port 30 is greater than the pressure in the particulate port 27, the first check valve 74 selectively closes for effectively sealing the first conduit 64 closed and inhibiting the gas from returning to the particulate container 20. Thus, even if the practitioner halts the vacuum stroke 70, the vacuum is maintained within the particulate container 20.

According to an exemplary embodiment, the plunger 36 of the vacuum device 18 may reverse direction to reset the plunger 36 for an additional vacuum stroke 70 to generate additional vacuum within the particulate container 20. The reverse direction is also referred to herein as a pressure stroke and is indicated by arrow 76 in FIG. 4B. To complete the pressure stroke 76 without forcing the gas back into the particulate container 20, the valve body 24 further includes a vent conduit 78 extending from the first conduit 64 to the ambient environment and a second check valve 80 to release excess pressure from the first passage 65. The second check valve 80 is fluidly connected to the first passage 65 and, more particularly, is mounted within the vent conduit 78 that opens into the first conduit 64. At this position, the second check valve 80 is operable to open and close by the pressure differential between the vacuum port 30 and the ambient environment. In the event that pressure in the vacuum port 30 is less than an ambient pressure in the ambient environment, the second check valve 80 selectively closes for sealing the first conduit 64 from the ambient environment. However, in the event that the pressure in the vacuum port 30 is greater than the ambient pressure, the second check valve 80 selectively opens for releasing excess pressure from the first passage 65 to the ambient environment, as indicated by arrow 81. By way of example, the first and second check valves 74, 80 are duckbill check valves. However, it will be appreciated that generally any type of check valve may be used as described above. For example, the first and/or second check valve 74, 80 may alternatively be a mushroom check valve, an umbrella check valve, a ball check valve, a dome check valve, a flapper valve, or any other type of check valve for permitting one-directional flow. As such, the invention is not intended to be limited to the exemplary valves shown and described herein.

Figure 4B:
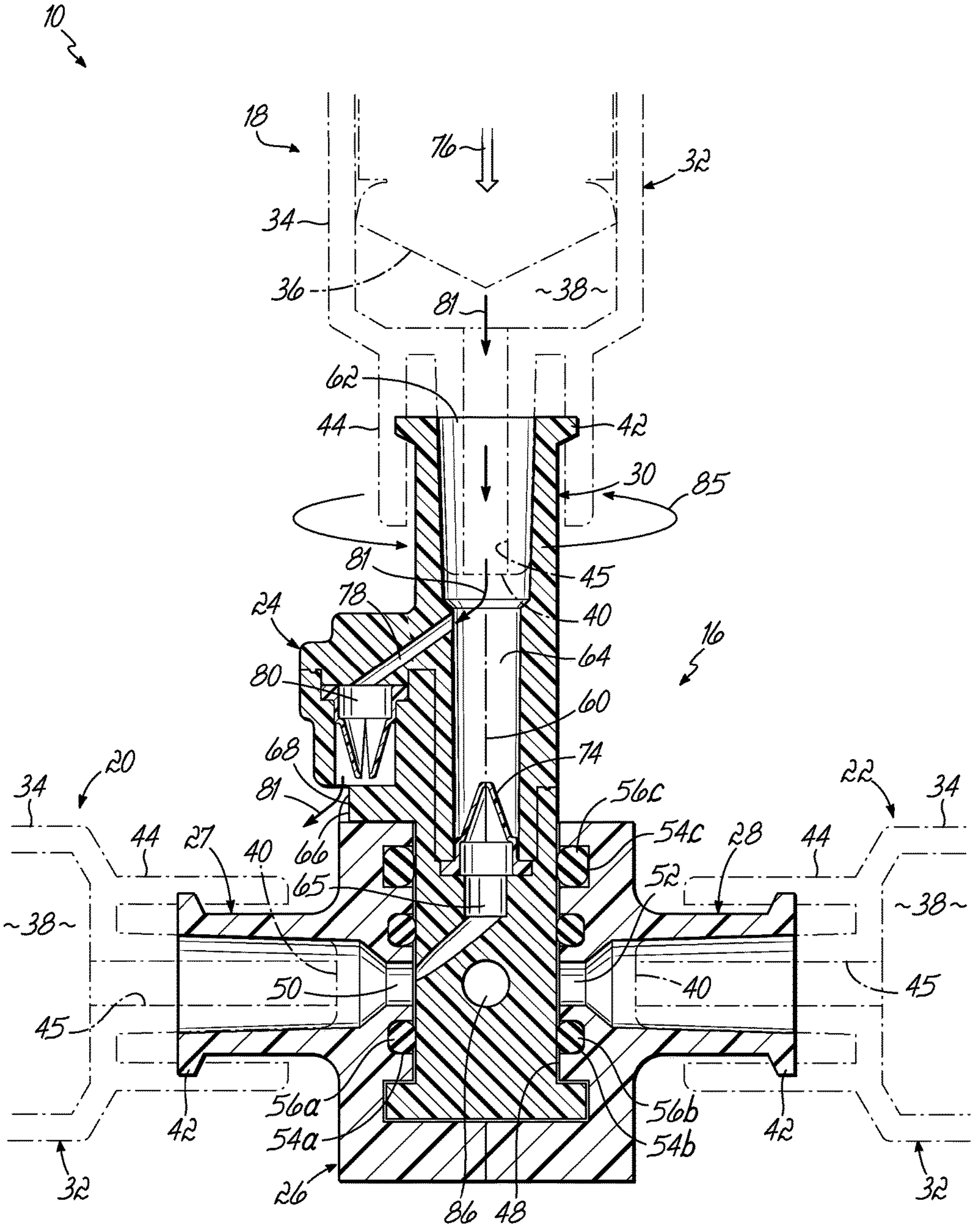
FIG. 4B is a cross-section view similar to FIG. 4A, but showing the showing the gas being discharged to the ambient environment.

An exemplary embodiment shown in FIG. 4A and FIG. 4B generates the vacuum for withdrawing the gas from the particulate container 20 via the plunger 36 cooperating with the syringe body 34 of the vacuum device 18. The practitioner may select or manufacture the particulate biomaterial, such as the bone graft material, using known devices and methods and then load the particulate container 20 with a desirable amount of the particulate biomaterial.

During the vacuum stroke 70, the plunger 36 moves distally from the valve 16, which, in turn, causes the volume of the cavity 38 proximal of the plunger 36 to increase. The increase in volume creates a decrease in pressure, otherwise referred to herein as the vacuum. The vacuum within the cavity 38 transfers to the first conduit 64 to simultaneously open the first check valve 74 and close the second check valve 80. With the first check valve 74 open, the vacuum transfers through the first conduit 64, the particulate bore 50, the particulate port 27 and throughout the fluidly connected particulate container 20. Because the particulate biomaterial and the gas within the particulate container 20 are exposed to the vacuum, the gas is withdrawn from the particulate container 20 through the first passage 65 and into to the increasing volume of the vacuum device 18.

The vacuum may continue to increase within the particulate container 20 so long as the plunger 36 of the vacuum device 18 moves distally through the vacuum stroke 70. Once the plunger 36 reaches the top of the vacuum stroke 70, the vacuum device 18 ceases to withdraw the gas from the particulate container 20. As such, the pressure within the particulate port 27 is below the pressure within the vacuum port 30 causing the first check valve 74 to close and generally maintain the vacuum within the particulate container 20.

Once the plunger 36 is at the top of the vacuum stroke 70, the cavity 38 may be purged of gas by manipulating the plunger 36 through the pressure stroke 76. Through the pressure stroke 76, the plunger 36 moves proximally toward the valve 16 through the cavity 38, which, in turn, causes the volume within the syringe body 34 to decrease. The decrease in volume creates an increase in pressure within the vacuum port 30 and the first conduit 64. While the first check valve 74 remains closed during the increase in pressure, the second check valve 80 opens with the increase in pressure and raises above that of the ambient environment. As such, the gas within the cavity 38 is forced by the plunger 36 from the cavity 38, into the vent conduit 78, through the second check valve 80, and into the ambient environment. The gas continues to purge from the cavity 38 until the plunger 36 reaches the bottom of the pressure stroke 76. The vacuum stroke 70 and pressure stroke 76 may be repeated to increase the vacuum within the particulate container 20 as desired by the practitioner or as limited by the sealing capabilities of the plunger 36, syringe body 34, and/or seals 56*a*, 56*b*, 56*c*. According to an exemplary embodiment, the vacuum device 18 is a 5 milliliter syringe that generates a vacuum between 0 inHg and 25 inHg. More particularly, the vacuum device 18 generates a vacuum of approximately 20 inHg for withdrawing the gas from the particulate biomaterial.

Figure 4C:
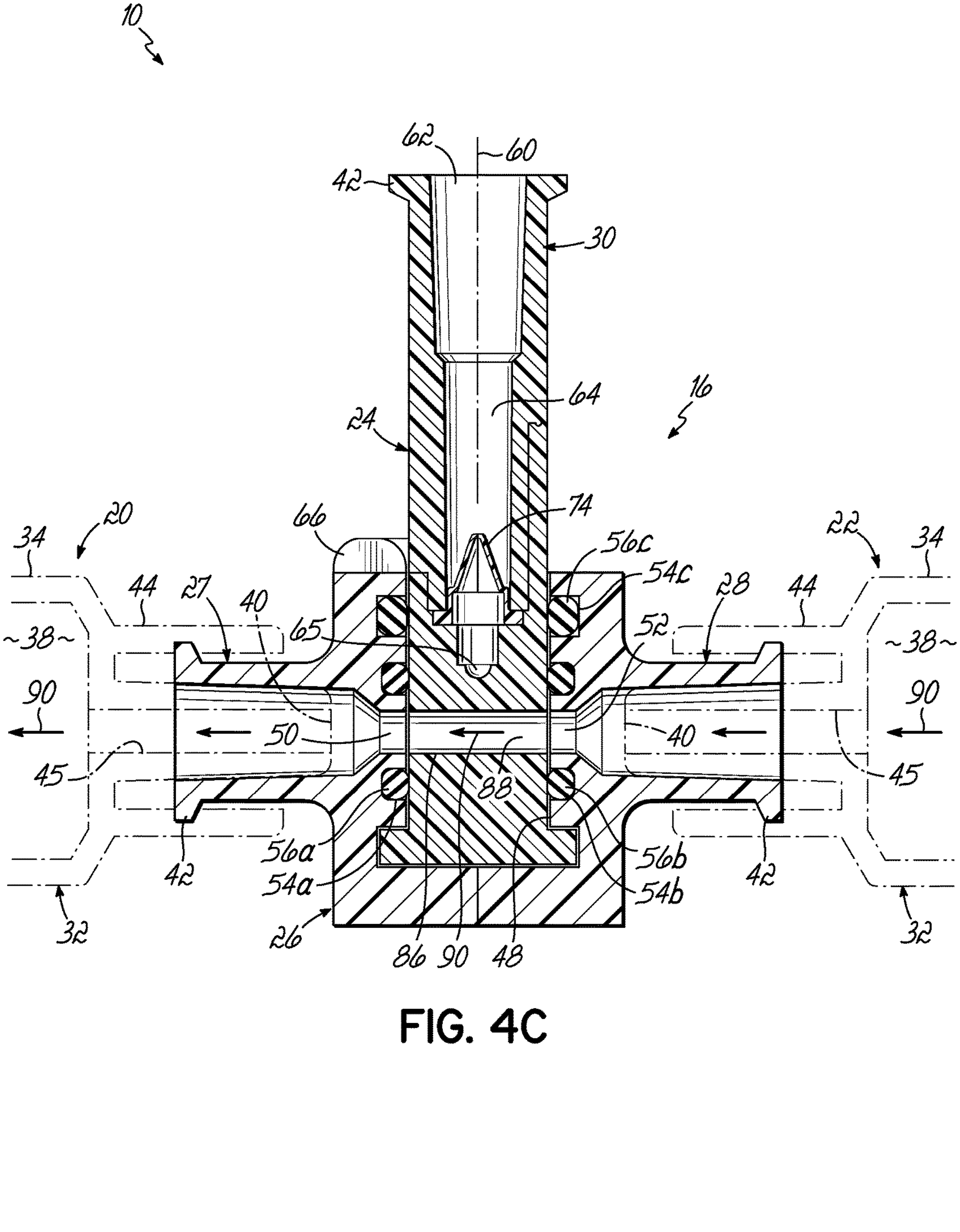
FIG. 4C is a cross-section view similar to FIG. 4B, but showing the valve body in a second position for introducing the liquid bone graft material into the particulate container.

With a desirable vacuum generated within the particulate container 20, the practitioner selectively moves the valve body 24 to the second position to fluidly disconnect the first conduit 64 from the particulate port 27. The hub 26 includes a second abutment member 82 (see FIG. 2) projecting distally toward the valve body 24 that cooperates with a second stop surface 84 (see FIG. 2) for positioning the valve body 24. More particularly, the valve body 24 rotates the counterclockwise direction until the second stop surface 84 contacts the second abutment member 82, as indicated by arrow 85. Accordingly, a second conduit 86 defined by the valve body 24 rotatably aligns to fluidly connect the particulate port 27 to the liquid port 28 and define a second passage 88 as shown in FIG. 4C. The second conduit 86 extends directly between the particulate bore 50 and the liquid bore 52 such that the liquid port 28, the liquid bore 52, the particulate bore 50, and the particulate port 27 collectively define the second passage 88 for introducing the liquid biomaterial into the particulate container 20, as indicated by arrows 90.

As discussed above and with reference to FIG. 3 and FIG. 4C, prior to moving the valve body 24 to the second position, the particulate container 20 contains the particulate biomaterial under the influence of the vacuum maintained therein. Thus, moving the valve body 24 to the second position releases the vacuum through the second passage 88 and to the liquid container 22. Because the liquid container 22 has a variable volume for containing the liquid biomaterial within the syringe body 34 of the liquid container 22, the vacuum released to the liquid container 22 collapses the variable volume and withdraws the liquid biomaterial from the liquid container 22, through the second passage 88, and into the particulate container 20. In the event that the particulate biomaterial is relatively porous, the vacuum tends to increase the rate of absorption of the liquid biomaterial within the particulate biomaterial and more quickly hydrate the particulate biomaterial to form a mixture of biomaterials.

Figure 5:
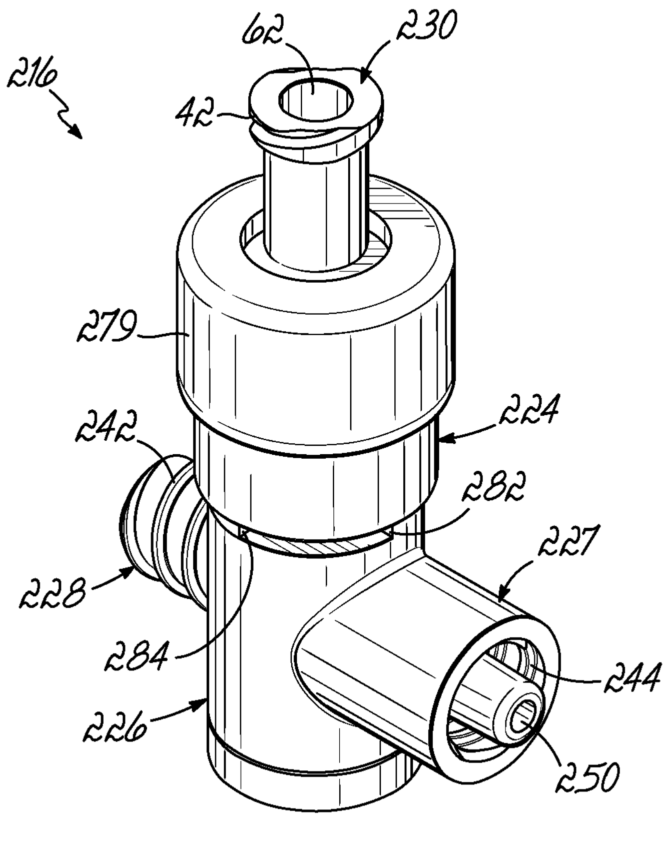
FIG. 5 is a perspective view of a second embodiment of a valve for hydrating a particulate bone graft material with a liquid bone graft material.
Figure 6A:
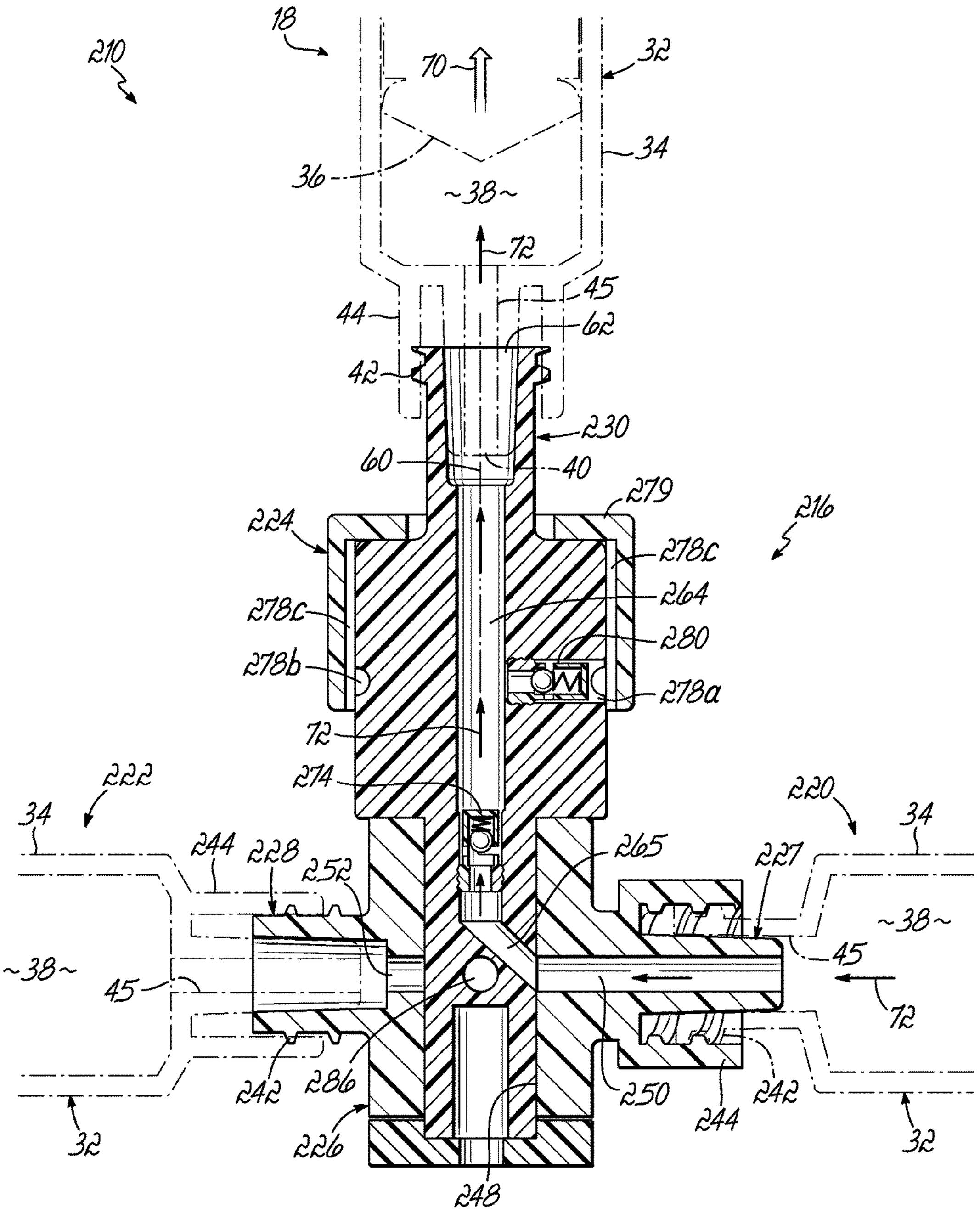
FIG. 6A is a cross-section of the valve of FIG. 5 having a valve body in a first position for withdrawing a gas from a particulate container.
Figure 6B:
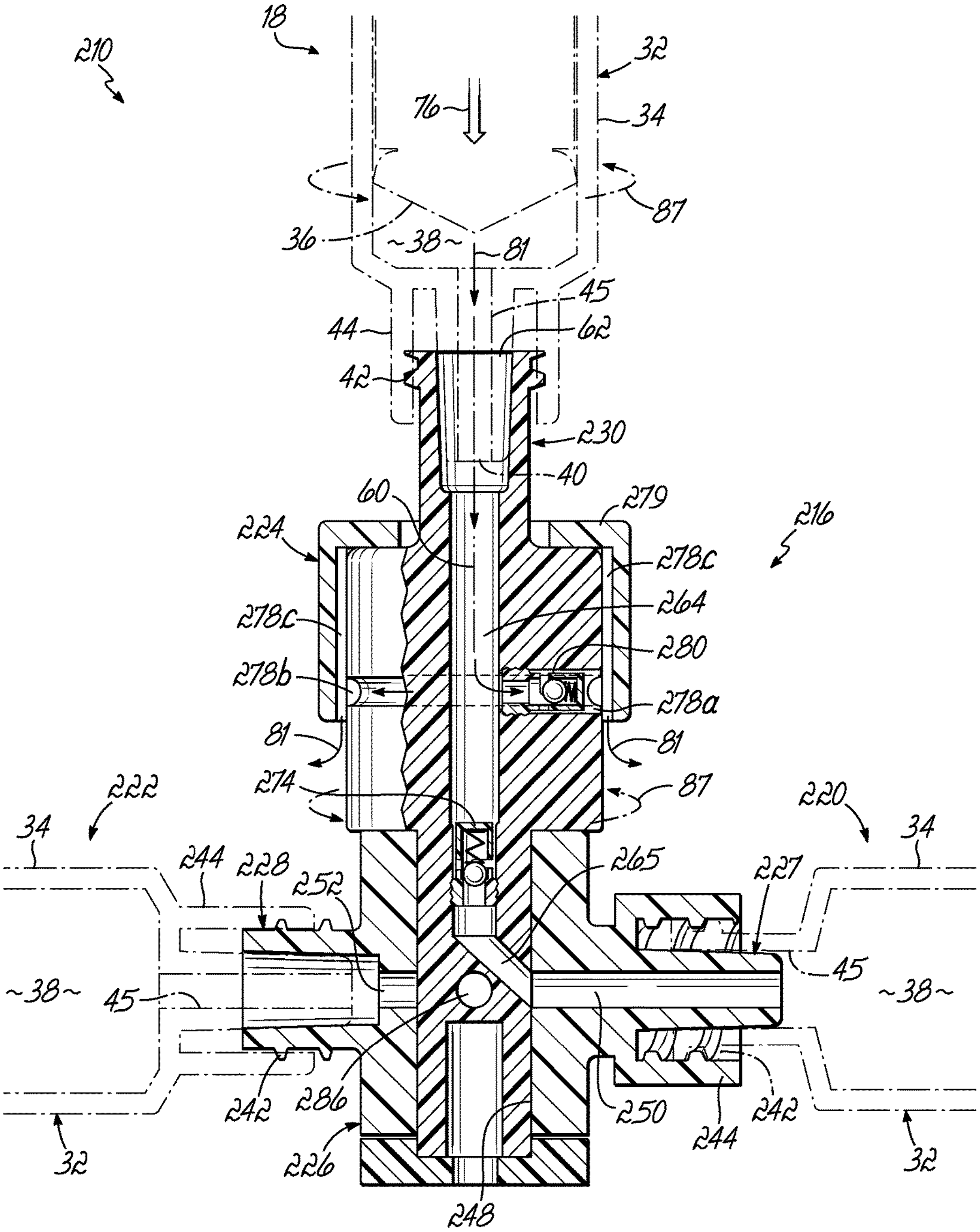
FIG. 6B is a cross-section view similar to FIG. 6A, but showing the showing the gas being discharged to the ambient environment.
Figure 6C:
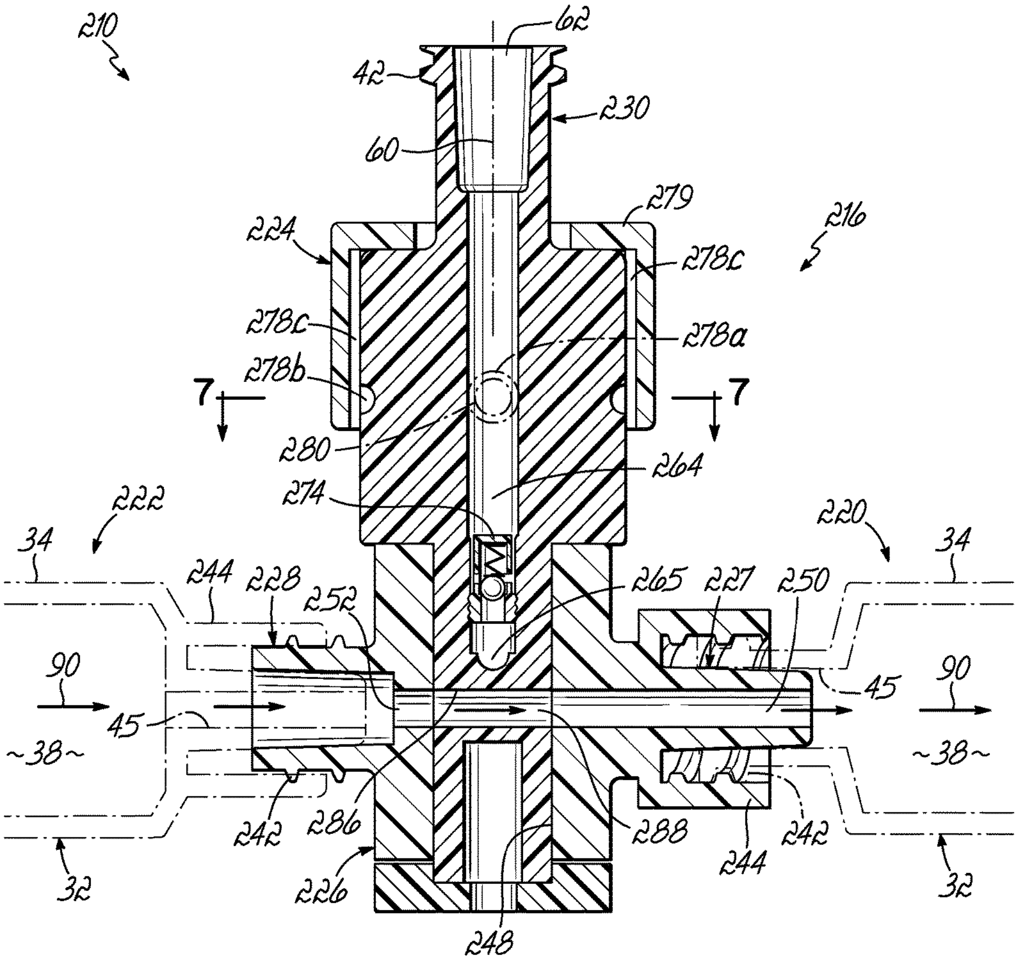
FIG. 6C is a cross-section view similar to FIG. 6B, but showing the valve body in a second position for introducing the liquid bone graft material into the particulate container.
Figure 7:
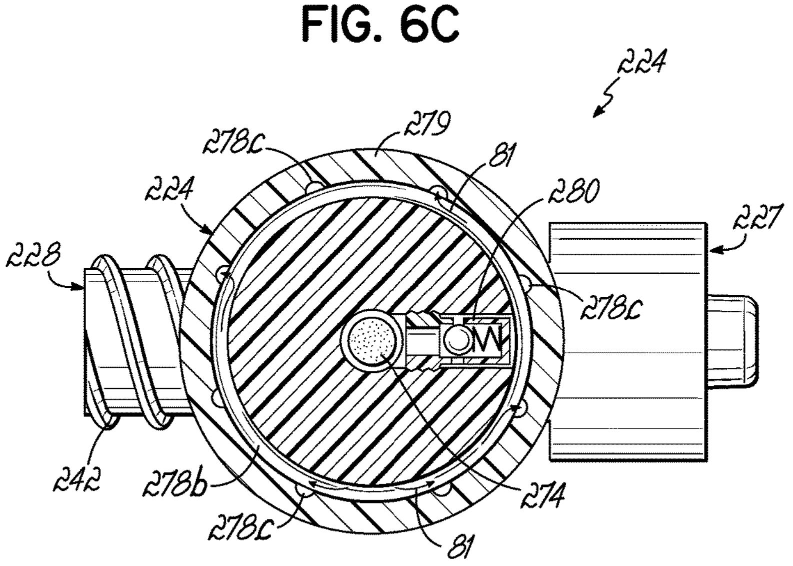
FIG. 7 is a cross-section view of the valve taken along section line 7-7 of FIG. 6C.

With reference to FIGS. 5-7, a second embodiment of an apparatus 210 for hydrating a particulate biomaterial with a liquid biomaterial includes a valve 216 fluidly connected to the vacuum device 18, a particulate container 220, and a liquid container 222. The particulate container 220 holds the particulate biomaterial, while the liquid container 222 holds the liquid biomaterial. In contrast with the previous embodiment, the liquid container 222 includes a female coupling 244, which cooperates with a liquid port 228 having a male coupling 242, while the particulate container 220 includes the male coupling 242 and a particulate port 227 has the female coupling 244. With respect to the second embodiment of the apparatus 210, like numbers indicate like features discussed above and it will be appreciated that the above description similarly applies to the apparatus 210.

The valve 216 includes a valve body 224 movably coupled with a hub 226 and, as such, selectively moves between a first position and a second position. According to an exemplary embodiment, the hub 226 includes the particulate port 227 and the opposing liquid port 228. The valve body 224 includes a vacuum port 230 configured to removably connect to the vacuum device 18 for generating a vacuum therein. The hub 226 surrounds a portion of the valve body 224 such that vacuum port 230 projects distally from the hub 226 and toward the vacuum device 18. More particularly, the hub 226 defines an aperture 248 that receives and captures the valve body 224 and defines a particulate bore 250 and a liquid bore 252. The particulate bore 250 extends from the particulate port 227 to an aperture 248, and the liquid bore 252 similarly extends from the liquid port 228 to the aperture 248. While the valve body 224 is captured within the aperture 248 of the hub 226, the valve body 224 is still free to rotate a clockwise direction, as indicated by arrow 53 (see FIG. 1), toward the first position and counterclockwise direction toward the second position.

To inhibit leakage between the hub 226 and the valve body 224 and into the aperture 248, an exemplary embodiment of the hub 226 and the valve body 224 are manufactured from one or more materials that fluidly seal against each other with the valve body 224 captured within the hub 226. For example, the hub 226 is manufactured from a first material that is relatively hard, while the valve body 224 is manufactured from a second material that is relatively soft. As such, the valve body 224 is sized relative to the aperture 248 to be compressed therein for sealing against the hub 226. More particularly, the first material of the hub 226 is polycarbonate, and the second material of the valve body 224 is polypropylene. As such, the first and second materials inhibit the vacuum, the particulate biomaterial, and the liquid biomaterial from leaking into the aperture 248 and/or into the ambient environment.

FIG. 6A shows the apparatus 210 having the valve body 224 in the first position. The valve body 224 extends along the rotational axis 60 and includes the distal opening 62 that opens into the vacuum port 230. The valve body 224 further defines a first conduit 264 that extends from the vacuum port 230 to the particulate bore 250 for fluid communication with the particulate port 227. As such, the vacuum port 230 and the particulate port 227 are fluidly connected only when the valve body 224 is in the first position. As discussed above, the valve body 224 is already in the first position and, as such, the vacuum port 230, the first conduit 264, the particulate bore 250, and the particulate port 227 collectively define a first passage 265 extending from the vacuum device 18 to the particulate container 20. However, in the event that the valve body 224 is not in the first position, the hub 226 includes a first abutment member (not shown) projecting distally toward the valve body 224 that cooperates with a first stop surface (not shown) for positioning the valve body 224. More particularly, the valve body 224 rotates the clockwise direction 53 (see FIG. 1) until the first stop surface (not shown) contacts the first abutment member (not shown) such that the first conduit 264 rotatably aligns to fluidly connect to the particulate port 227 and define the first passage 265.

As discussed above in greater detail, the vacuum stroke 70 generates the vacuum, as indicated by arrows 72, and the pressure stroke 76 for releasing the gas to the ambient environment. However, rather than the duckbill check valves 74, 80 shown in FIGS. 4A-4C, the valve 216 of FIGS. 5-7 includes stainless steel ball check valves 274, 280. In addition, to complete the pressure stroke 76 without forcing the gas back into the particulate container 20, the valve body 224 further includes a vent conduit 278*a* extending from the first conduit 264 to an annular channel 278*b* generally surrounding and at least partially defined by the valve body 224. The valve body 224 further includes a collar 279 further defining the annular channel 278*b*. The collar 279 also defines a plurality vent passages 278*c* in fluid communication between the annular channel 278*b* and the ambient environment. The second check valve 280 is positioned within the vent conduit 278*a* to release excess pressure from the first passage 265 to the annular channel 278*b*. From the annular channel 278*b*, the gas vents to the ambient environment through the plurality of vent passages 278*c* so that if the practitioner covers one or more of the vent passages 278*c* during the medical procedure, the gas still may be forced to the ambient environment through one of the uncovered vent passages 278*c*.

With respect to the second position, the hub 226 includes a second abutment member 282 projecting distally toward the valve body 224 that cooperates with a second stop surface 284. More particularly, the valve body 224 rotates the counterclockwise direction until the second stop surface 284 contacts the second abutment member 282, as indicated by arrow 85 of FIG. 6B. Accordingly, a second conduit 286 defined by the valve body 224 rotatably aligns to fluidly connect the particulate port 227 to the liquid port 228 and define a second passage 288 as shown in FIG. 6C.

The second passage 288 fluidly connects the particulate container 20 to the liquid container 222 for releasing the desirable vacuum to the liquid container 222 and withdrawing the liquid biomaterial therefrom, as indicated by arrows 90, and similarly discussed above. Thereby, the valve 216 is configured to hydrate the particulate biomaterial with the liquid biomaterial for forming the mixture of biomaterials for use during the medical procedure.

Figure 8A:
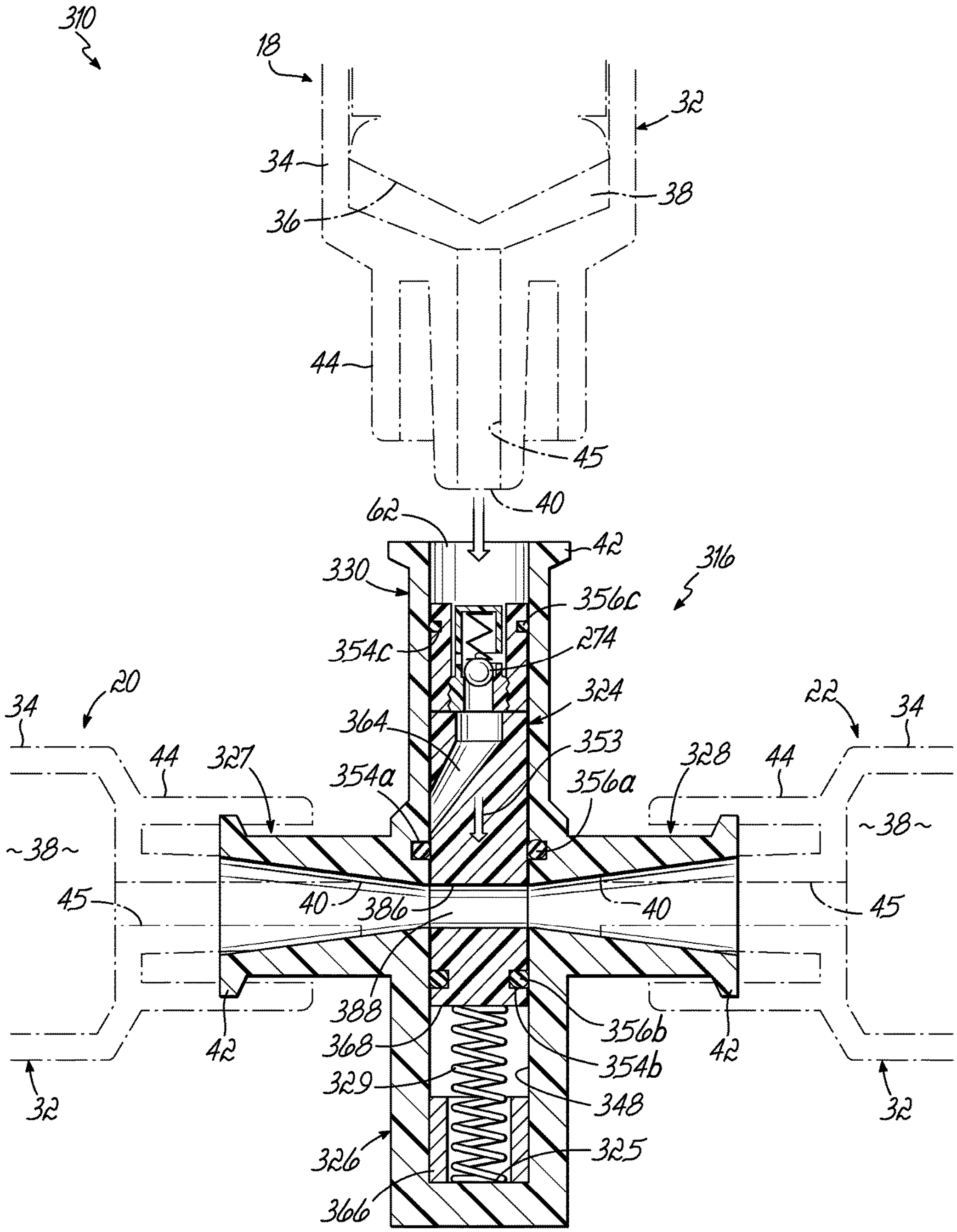
FIG. 8A is a cross-section of a third embodiment of a valve for hydrating a particulate bone graft material with a liquid bone graft material in which the valve has a valve body in a second position.
Figure 8B:
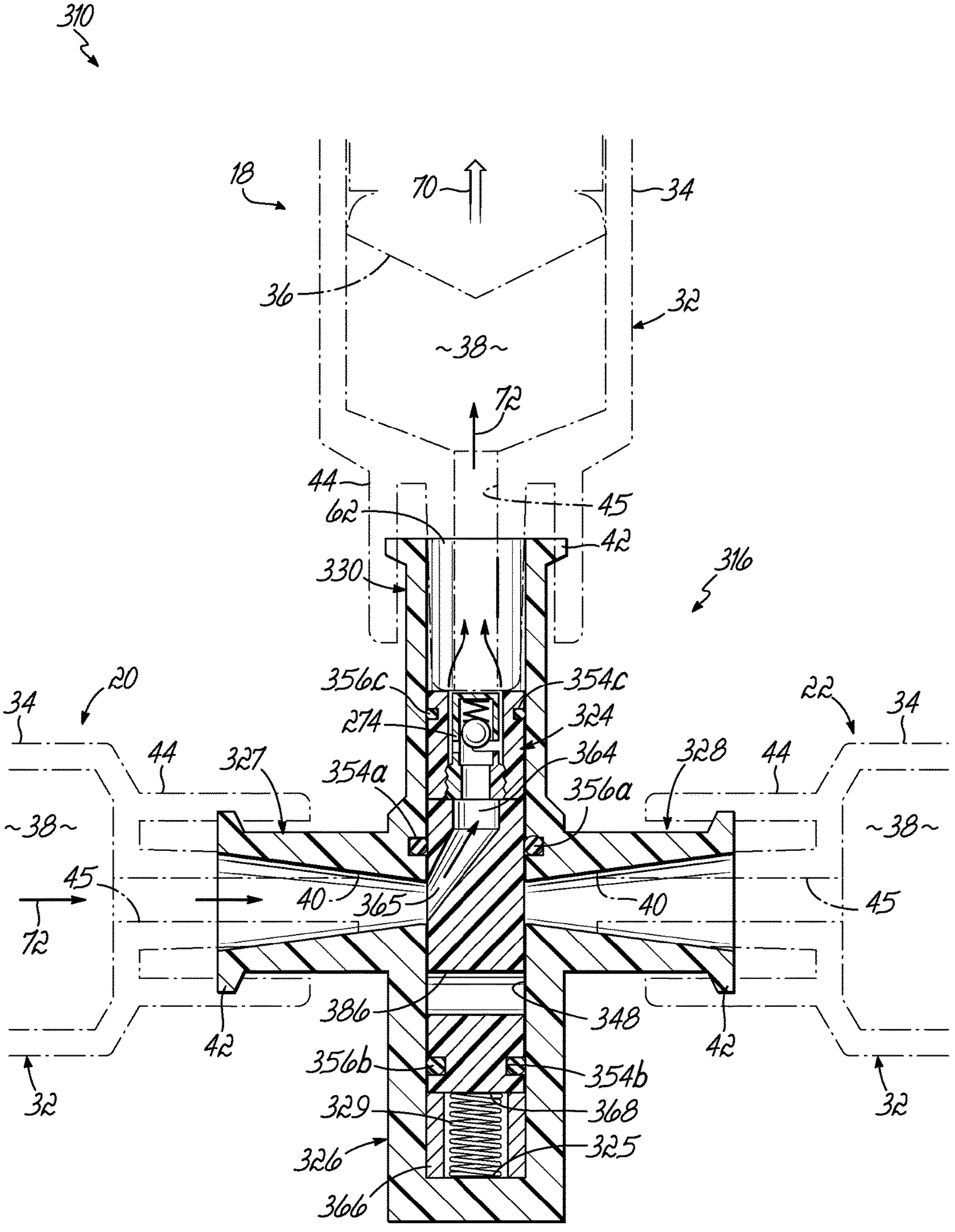
FIG. 8B is a cross-section view similar to FIG. 7A, but showing the valve having a valve body in a first position for withdrawing a gas from a particulate container.
Figure 8C:
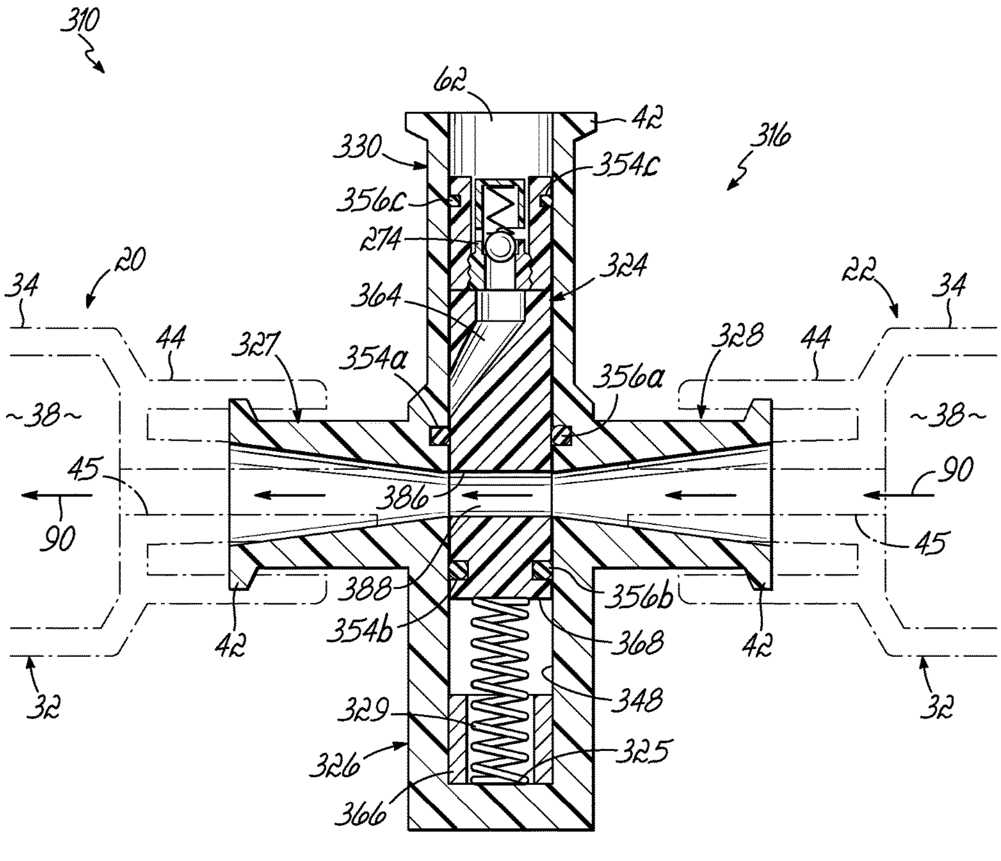
FIG. 8C is a cross-section view similar to FIG. 7B, but showing the valve body in the second position for introducing the liquid bone graft material into the particulate container.

With reference to FIGS. 8A-8C, a third embodiment of an apparatus 310 for hydrating a particulate biomaterial with a liquid biomaterial includes a valve 316 fluidly connected to the vacuum device 18, the particulate container 20, and the liquid container 22. The particulate container 20 holds the particulate biomaterial, while the liquid container 22 holds the liquid biomaterial. With respect to the third embodiment of the apparatus 310, like numbers indicate like features discussed above and it will be appreciated that the above description similarly applies to the apparatus 310.

The valve 316 includes a valve body 324 movably coupled with a hub 326 and, as such, selectively moves between a first position and a second position. According to an exemplary embodiment, the hub 326 includes a particulate port 327 and an opposing liquid port 328. In addition, the hub 326 includes a vacuum port 330 configured to removably connect to the vacuum device 18 for generating a vacuum therein. The hub 326 also defines an aperture 348 that receives the valve body 324 slidably therein. The valve body 324 is mounted to a bottom 325 via a biasing member 329, such as a spring, for being biased in the second position. Specifically, the valve body 324 linearly translates, as indicated by arrow 353, from the second position to the first position within the hub 326.

To inhibit leakage between the hub 326 and the valve body 324 and into the aperture 348, an exemplary embodiment of the hub 326 includes an annular recess 354*a* about the aperture 348 and positioned adjacent to the valve body 324 for distal sealing above the particulate and liquid ports 327, 328. The annular recess 354*a* receives a seal 356*a* configured to fluidly seal between the hub 326 and valve body 324 and inhibit leakage from the particulate and liquid ports 327, 328 through the vacuum port 330 and to the ambient environment. The valve body 324 also includes additional annular recesses 354*b*, 354*c* positioned adjacent to both ends of the valve body 324 for further sealing. The annular recess 354*b* is adjacent to the biasing member 329 that similarly receives another seal 356*b* that is configured to fluidly seal between the hub 326 and the valve body 324 and inhibit the leakage from the particulate and liquid ports 327, 328 toward the bottom 325 of the valve body 324. The annular recess 354*c* is positioned adjacent to the vacuum port 330 and receives a seal 356*c* for inhibiting leakage into the vacuum port 330. Collectively, the seals 356*a*, 356*b*, 356*c* inhibit the vacuum, the particulate biomaterial, and the liquid biomaterial from leaking into the aperture 348 and/or into the ambient environment.

As discussed briefly above, the valve body 324 is biased in the second position. However, by coupling the female coupling 44 of the vacuum device 18 to the vacuum port 330, the female coupling 44 engages the valve body 324 and forces the valve body 324 linearly to the first position as shown in FIG. 8B for withdrawing the gas from the particulate container 20. The hub 326 includes an abutment member 366 projecting from the bottom 325 and surrounding the biasing member 329 that cooperates with a stop surface 368 for positioning the valve body 224 in the first position. More particularly, the valve body 324 linearly translates into the aperture 348 until the stop surface 368 contacts the abutment member 366.

With respect to FIG. 8B, the valve body 324 extends linearly along the aperture 348, and the hub 326 includes the distal opening 62 that opens into the vacuum port 330. The valve body 324 defines a first conduit 364 that extends from the vacuum port 330 to the particulate port 327. As such, the vacuum port 330 and the particulate port 327 are fluidly connected only when the valve body 324 is in the first position. In the first position, the vacuum port 330, the first conduit 364, and the particulate port 327 collectively define a first passage 365 extending from the vacuum device 18 to the particulate container 20.

As discussed above in greater detail, the vacuum stroke 70 generates the vacuum, as indicated by arrows 72. However, rather than the duckbill check valve 74 shown in FIGS. 4A-4C, the valve 316 of FIGS. 8A-8C includes the stainless steel ball check valve 274 discussed above. While the third embodiment of the apparatus 310 does not include a second check valve for venting gas, such as during the pressure stroke 76 discussed above, it will be appreciated that such a check valve may be used with the apparatus 310, and the apparatus 310 is not intended to be limited to one check valve and/or one vacuum stroke 70.

Once the desirable vacuum is maintained within the particulate container 20, the practitioner disconnects the vacuum device 18 from the vacuum port 330 to allow the biasing member 329 to linearly translate the valve body 324 to the second position. In the second position, a second conduit 386 defined by the valve body 324 linearly aligns to fluidly connect the particulate port 327 to the liquid port 328 and define a second passage 388 as shown in FIG. 8C.

The second passage 388 fluidly connects the particulate container 20 to the liquid container 22 for releasing the desirable vacuum to the liquid container 22 and withdrawing the liquid biomaterial therefrom, as indicated by arrows 90, and similarly discussed above. Thereby, the valve 316 is configured to hydrate the particulate biomaterial with the liquid biomaterial for forming the mixture of biomaterials for use during the medical procedure.

In use, the practitioner removes the plungers 36 from the particulate container 20 and liquid container 22 shown in FIGS. 1-3 and loads each with the particulate biomaterial and the liquid biomaterial, respectively, during a medical procedure. Alternatively one or both of the particulate and liquid containers 20, 22 may be preloaded with a particular biomaterial and liquid biomaterial for the convenience of the practitioner. In any case, the particulate and liquid containers 20, 22 are each fluidly connected to the particulate and liquid ports 27, 28, respectively, via cooperating male and female couplings 42, 44. While the following describes the method of hydrating the particulate and liquid biomaterial primarily with respect to the first embodiment of the apparatus 10, it will be appreciated that additional embodiments may be similarly used.

The vacuum device 18, such as the syringe 32, is also fluidly connected to vacuum port 30 by connecting the male coupling 42 of the vacuum port 30 to the female coupling 44 of the vacuum device 18. According to an exemplary embodiment, the male and female couplings 42, 44 are male and female luer couplings 42, 44 that rotatably connect with the clockwise direction 53 and rotatably disconnect with the counterclockwise direction 85. Notably, the clockwise direction 53 for fluid connection of the vacuum device 18 is also the direction for moving the valve body 24 to the first position, and the counterclockwise direction 85 for fluid disconnection of the vacuum device 18 is also the direction for moving the valve body 24 to the second position. Accordingly, the practitioner is able to direct the valve body 24 to the first and second positions while simultaneously fluidly connecting and disconnecting the vacuum device 18, respectively, for simplifying the medical procedure.

In the first position, the vacuum device 18 fluidly connects to the particulate container 20 via the first passage 65, which is at least partially defined by the valve body 24. With respect to FIG. 4A and FIG. 4B, the practitioner manipulates the plunger 36 of the vacuum device 18 through the vacuum and pressure strokes 70, 76 as needed to generate the desirable vacuum within the particulate container 20 and vent the gas to the ambient environment as discussed above in greater detail. It will be appreciated, however, that the pressure stoke 76 is not necessary if the desirable vacuum within the particulate container 20 is generated during the initial vacuum stroke 70.

Once the desirable vacuum is maintained within the particulate container 20, the practitioner rotates the vacuum device 18 counterclockwise, as shown in FIG. 4B, to simultaneously disconnect the vacuum device 18 from the vacuum port 30 and rotate the valve body 24 to the second position, as shown in FIG. 4C. With respect to FIG. 4C, the first conduit 64 fluidly disconnects from the particulate port 27 and the second conduit 86 fluidly connects to the particulate port 27 to define the second passage 88. The second passage 88 fluidly connects the particulate and liquid containers 20, 22 in the second position to release the desirable vacuum within the particulate container 20 to the liquid container 22. The liquid biomaterial is thereby withdrawn from the liquid container 22 and forced into the particulate container 20 with the particulate biomaterial. Under the influence of the vacuum, the liquid biomaterial more quickly and uniformly absorbs throughout the particulate biomaterial to form a mixture of biomaterials. However, in the event that the liquid biomaterial fails to uniformly absorb throughout the particulate biomaterial, the practitioner may also manipulate the plungers 36 of both the particulate and liquid containers 20, 22 cooperatively to force the mixture of biomaterials back and forth between both containers 20, 22. In doing so, the mixture of biomaterials is agitated by passing back and forth through the second passage 88 for blending the mixture of biomaterials uniformly.

The practitioner disconnects one or both of the particulate and liquid containers 20, 22 containing the mixture of biomaterials from the hub 26. To dispense the mixture of biomaterials, the practitioner then manipulates the plunger 36 to force the mixture of biomaterials from the syringe body 34. According to an exemplary embodiment, the mixture of biomaterials includes bone graft materials, and, as such, is dispensed onto an anatomical site of a patient during a medical procedure.

While the present invention has been illustrated by the description of one or more embodiments thereof, and while the embodiments have been described in considerable detail, they are not intended to restrict or in any way limit the scope of the appended claims to such detail. The various features shown and described herein may be used alone or in any combination. Additional advantages and modifications will readily appear to those skilled in the art. The invention in its broader aspects is therefore not limited to the specific details, representative apparatus and method and illustrative examples shown and described. Accordingly, departures may be from such details without departing from the scope of the general inventive concept.

What is claimed is:

1. A method of hydrating a particulate biomaterial held within a particulate container with a liquid biomaterial held within a liquid container to form a mixture of biomaterials, the method using a vacuum device and a valve, the valve being fluidly connected to the particulate container, the liquid container, and the vacuum device, the valve having a valve body configured to selectively move between a first position and a second position, and having a check valve provided within the valve body, the method comprising:

generating a vacuum within the particulate container with the vacuum device when the valve body is in the first position;

withdrawing a gas from the particulate container and through the valve body and the check valve toward the vacuum device to maintain the vacuum within the particulate container;

moving the valve body to the second position such that the liquid container fluidly connects to the particulate container via the valve body;

releasing the vacuum within the particulate container to the liquid container to withdraw the liquid biomaterial from the liquid container and introduce the liquid biomaterial into the particulate container; and hydrating the particulate biomaterial with the liquid biomaterial to form the mixture of biomaterials.

2. The method of claim 1, wherein hydrating the particulate biomaterial further comprises forcing the mixture of biomaterials from the particulate container, through the valve body, and to the liquid container to blend the mixture of biomaterials.

3. The method of claim 1, further comprising connecting the vacuum device to the valve while simultaneously directing the valve body toward the first position.

4. The method of claim 1, further comprising disconnecting the vacuum device from the valve while simultaneously directing the valve body toward the second position.

5. The method of claim 1, wherein the particulate biomaterial and the liquid biomaterial comprise bone graft materials.

6. The method of claim 5, further comprising dispensing the mixture of the bone graft materials onto an anatomical site during a medical procedure.

7. The method of claim 1, wherein moving the valve body to the second position comprising rotating the valve body to the second position.

8. The method of claim 7, wherein:

the valve body defines a vacuum port, and comprising rotating the valve body to the second position comprises disconnecting the vacuum port from the vacuum device.

9. The method of claim 1, wherein moving the valve body to the second position comprises linearly translating the valve body to the second position.

10. The method of claim 1, wherein:

the vacuum device is a first syringe comprising a first syringe body and a first piston, and generating the vacuum within the particulate container with the vacuum device comprises withdrawing the first piston within the first syringe body.

11. The method of claim 10, wherein the particulate container is a second syringe configured to hold the particulate biomaterial.

12. The method of claim 11, wherein the liquid container is a third syringe configured to hold the liquid biomaterial.

13. The method of claim 1, wherein:

the valve further comprises a hub, and the method further comprises movably coupling the valve body to the hub to selectively move between the valve body between the first position and the second position.

14. The method of claim 1, wherein the check valve is a first check valve, and the valve further comprises a second check valve in fluid communication with a passage of the vacuum device and an ambient environment.

15. A method of hydrating a particulate biomaterial held within a particulate container with a liquid biomaterial held within a liquid container to form a mixture of biomaterials, the method using a vacuum device and a valve, the valve being fluidly connected to the particulate container, the liquid container, and the vacuum device, the valve having a valve body configured to selectively move between a first position and a second position, and having a first check valve and a second check valve, the second check valve in fluid communication with a passage of the vacuum device and an ambient environment, the method comprising:

generating a vacuum within the particulate container with the vacuum device when the valve body is in the first position;

withdrawing a gas from the particulate container and through the valve body and the first check valve toward the vacuum device to maintain the vacuum within the particulate container;

discharging the gas from the passage and through the second check valve into the ambient environment when the valve body is in the first position;

moving the valve body to the second position such that the liquid container fluidly connects to the particulate container via the valve body;

releasing the vacuum within the particulate container to the liquid container to withdraw the liquid biomaterial from the liquid container and introduce the liquid biomaterial into the particulate container; and hydrating the particulate biomaterial with the liquid biomaterial to form the mixture of biomaterials.

16. The method of claim 15, wherein hydrating the particulate biomaterial further comprises forcing the mixture of biomaterials from the particulate container, through the valve body, and to the liquid container to blend the mixture of biomaterials.

17. The method of claim 15, wherein moving the valve body to the second position comprises rotating the valve body to the second position.

18. The method of claim 17, wherein:

the valve body defines a vacuum port, and rotating the valve body to the second position comprises disconnecting the vacuum port from the vacuum device.

19. The method of claim 15, wherein moving the valve body to the second position comprises linearly translating the valve body to the second position.

20. The method of claim 15, wherein:

the valve further comprises a hub, and the method further comprises movably coupling the valve body to the hub to selectively move between the valve body between the first position and the second position.

* * * * *